United States Patent
Bahnisch

(10) Patent No.: US 6,894,081 B2
(45) Date of Patent: May 17, 2005

(54) METHOD FOR CATALYTIC PRODUCTION OF METHANOL AND A DEVICE FOR IMPLEMENTING SAID METHOD

(75) Inventor: Hans-Joachim Bahnisch, Dortmund (DE)

(73) Assignee: Uhde GmbH, Dortmund (DE)

( * ) Notice: Subject to any disclaimer, the term of this patent is extended or adjusted under 35 U.S.C. 154(b) by 0 days.

(21) Appl. No.: 10/495,700
(22) PCT Filed: Oct. 19, 2002
(86) PCT No.: PCT/EP02/11718
§ 371 (c)(1), (2), (4) Date: May 14, 2004
(87) PCT Pub. No.: WO03/042144
PCT Pub. Date: May 22, 2003

(65) Prior Publication Data
US 2005/0020700 A1 Jan. 27, 2005

(30) Foreign Application Priority Data
Nov. 16, 2001 (DE) .......................... 101 56 092

(51) Int. Cl.⁷ .............................................. C07C 27/00
(52) U.S. Cl. ...................... 518/713; 518/700; 518/706; 518/722
(58) Field of Search ................................ 518/700, 713, 518/706, 722

(56) References Cited

U.S. PATENT DOCUMENTS

| | | |
|---|---|---|
| 2,904,575 A | 9/1959 | Peet |
| 5,523,326 A | 6/1996 | Dandekar et al. |
| 6,090,312 A | 7/2000 | Ziaka |

FOREIGN PATENT DOCUMENTS

| | | |
|---|---|---|
| EP | 0 200 880 A | 11/1986 |
| JP | 59109589 A | 6/1984 |

Primary Examiner—J. Parsa
(74) Attorney, Agent, or Firm—Marshall & Melhorn, LLC

(57) ABSTRACT

Process for the catalytic production of methanol under pressure using a synthesis gas which at least contains hydrogen, carbon monoxide, carbon dioxide and also undesired impurities, with at least one stage being equipped with a reactor, in which an absorption stage is connected upstream of each catalytic reaction system for the production of methanol, which contains catalyst material suitable as absorbent for the synthesis of methanol, the absorption stage being operated at a temperature which is below the temperature required for the catalytic conversion to methanol.

6 Claims, 1 Drawing Sheet

METHOD FOR CATALYTIC PRODUCTION OF METHANOL AND A DEVICE FOR IMPLEMENTING SAID METHOD

BACKGROUND OF THE INVENTION

The present invention relates to a process for the catalytic production of methanol and to a unit for running the process. Similar processes for the catalytic production of methanol were presented over the past years, patent numbers DE 21 17 060, DE 25 29 591, DE 32 20 995, DE 35 18 362, U.S. Pat. No. 2,904,575 and DE 41 00 632 being referred to as examples for the great variety of technical solutions.

Technologies of this kind generally use a suitable synthesis gas which predominantly contains constituents such as carbon monoxide, carbon dioxide and hydrogen, but also minor amounts of vapour, nitrogen, methane, ammonia, ethene, ethyne, hydrogen cyanide, oxygen, sulphur compounds, chlorine compounds, iron compounds, especially iron carbonyls, elementary carbon, especially carbon black particles, metal compounds of vanadium, potassium, sodium and nickel as well as solid particles in the form of dust. Such a synthesis gas is usually fed at a pressure of approx. 40 to 100 bar to a reaction system of several reactors which are arranged either in a cascade and/or in a loop system, as a rule being provided with a catalyst inventory and a device for heat dissipation. In each of the reactors, a partial conversion to methanol is achieved at a temperature of more than 200° C., said methanol being condensed and purified downstream of the respective reactor. The reaction heat released from the catalyst bed of the reactors is utilised for the production of steam which can be used for other applications, tube bundles being provided for this purpose in the catalyst bed and being fed with boiler feed water that evaporates in these pipelines.

The catalysts selected are special copper-based types but they involve the disadvantage to be very expensive, extremely sensitive to catalytic poison and to trigger an increasing number of secondary reactions at high temperatures which produce ethanol, butyl alcohol and dimethyl ether, and under relatively high working temperatures, the copper-based crystallites will act catalytically and cause a rearrangement to form larger crystals of a smaller specific surface and thus reduce the catalyst activity specific to space.

The engineer commissioned to construct a plant for methanol production is therefore confronted with the problem to ensure long service life for the reactors to meet the rated methanol production capacity by adequately dimensioning the catalyst volume and by providing sophisticated equipment for the removal of catalyst poison from the synthesis gas. This is usually achieved by calculating the required catalyst volume with a wide safety margin which accordingly increases the specific investment cost.

The operator of a plant for the methanol production is consequently confronted with the problem that the activity of the catalyst is subject to considerable variations throughout the service life of the catalyst. At the beginning of a production cycle, the fresh catalyst material packed is very active and requires to permanently counteract the danger of a reaction beyond control, i.e. by operating the steam generation, which moderates the reaction, at a lower temperature and a lower pressure which will result in a deterioration of the steam quality. An other option is to perform an adequate synthesis gas rarefaction using inert components, but this involves the disadvantage of higher equipment costs for the compression. If the methanol synthesis took place without being adequately moderated, the temperatures in the reactors would rise to such an extent that it might stimulate the formation of secondary products and cause faster catalyst ageing due to crystallite rearrangement.

As the production cycle proceeds, the catalyst layers next to the synthesis gas are gradually poisoned due to the existing traces of catalyst poison. Such poisoning takes place in different ways: On the one hand, sulphur and chlorine compounds as well as ammonium will cause a chemical deactivation of the catalytically active catalyst components. On the other hand, solid particles deposit on the surface of the catalyst and thus form a layer which inhibits diffusion. In addition, iron or nickel carbonyl compounds as well as other metal compounds liberated for example by corrosion (rust) or abrasion from the pipelines or other plant construction materials may change the catalytic system itself and thus contribute to the catalysis of other undesired end products. Since all of these poisonous effects are irreversible, the whole catalyst packing cannot be regenerated and must be disposed of after use.

In a first step, the plant operator may counteract the gradual poisoning by raising the partial pressure of the components involved in the reaction and in a further step he may increase the overall pressure, which in turn will result in the need for additional compression capacity; and in a final step he may raise the reaction temperature by augmenting the pressure and temperature of the moderating steam. The final step, however, accelerates the ageing process of said part of the catalyst bed that was not poisoned before and thus produces the undesired secondary products mentioned above. Hence, it has been of primary interest for years that a solution to this problem be provided by plant construction companies to the benefit of plant operators.

The aim of the present invention is to overcome the described problems by a cost-efficient technological solution.

SUMMARY OF THE INVENTION

This aim is achieved by arranging an absorption stage upstream of each catalytic reaction system intended for methanol production, the absorbent being constituted by a catalyst material suitable for the synthesis of methanol and the absorption stage being operated at a temperature which is below the temperature required for the catalytic conversion to methanol.

The absorption stage operates in such a manner that the catalyst poisons which would spoil the downstream catalyst required for methanol synthesis, precipitate instead on the upstream catalyst material and are thus separated by absorption. The advantage is that the downstream catalyst will not be poisoned and the plant engineer must not provide for a wide safety margin when calculating the catalyst volume required in the methanol synthesis reactor. A further outcome is that the requirements to be met by the synthesis gas purification are less stringent, the engineer being forced to weigh between the investment cost for the absorption stage and the cost for the synthesis gas purification.

The plant operator hence disposes of an operating mode that is much more uniform and cost-efficient throughout the whole catalyst life of the methanol synthesis reactors, not to speak of the considerable extension of the catalyst service life.

Since the catalyst material used as absorbent need not meet any demands for the selectivity of the conversion rates, said rate being zero in the ideal case, a low-cost catalyst material may be used as absorbent, for example with the following composition: 30 to 50% CuO, 30 to 50% ZnO and 10 to 30% $Al_2O_3$, which is another advantage of the present invention.

When the working temperature is selected for the absorption stage, the only aspect to be considered is that poisoning reactions may in fact take place but triggering of the methanol synthesis reaction is for sure avoided. This is ensured by setting the temperature to a range between 100° C. and 200° C., the preferred absorption temperature being 150° C.

The absorption stage may be of simple design because there is no necessity for any heat dissipation device as required in the methanol synthesis reactors, one design option being a simple cylindrical vessel provided with internals that accommodate the catalyst inventory and permit an axial or radial gas flow through the bed, and with one gas inlet and one gas outlet at each end as well as with a catalyst feed and discharge facility. A favourable option is to use two parallel-connected vessels each of which can be shut off on the gas side independently of the other so that catalyst material can be loaded or discharged and the absorption material be replaced while the unit remains in operation.

It is recommended that the absorption stage be installed in the direct vicinity of the synthesis reactor, a preferred arrangement being the separation of both equipment items merely by means of a heat exchanger which raises the temperature of the synthesis gas to the level required for the synthesis. It is of course possible to install the absorption stage upstream or downstream of the compression stage which supplies the pressure required for the methanol synthesis, and this may be a useful measure especially in a unit that has a large number of reactors for the methanol synthesis. It may also be adequate to combine these two options by providing a central absorption stage which absorbs the major part of the catalytic poisons and by arranging further absorption stages to be installed upstream of each methanol reactor for safety reasons, in particular if the process configuration provides for external gas streams that are admixed to the synthesis gas downstream of the compression unit but upstream of the synthesis gas reactors, and if the construction materials selected cause corrosion and consequently peeling-off of metal chips must be expected in the section between the compression unit and the methanol reactors.

BRIEF DESCRIPTION OF THE DRAWINGS

Details of the present invention are illustrated by means of a process diagram FIG. 1.

DESCRIPTION OF THE PREFERRED EMBODIMENT

Figure 1:
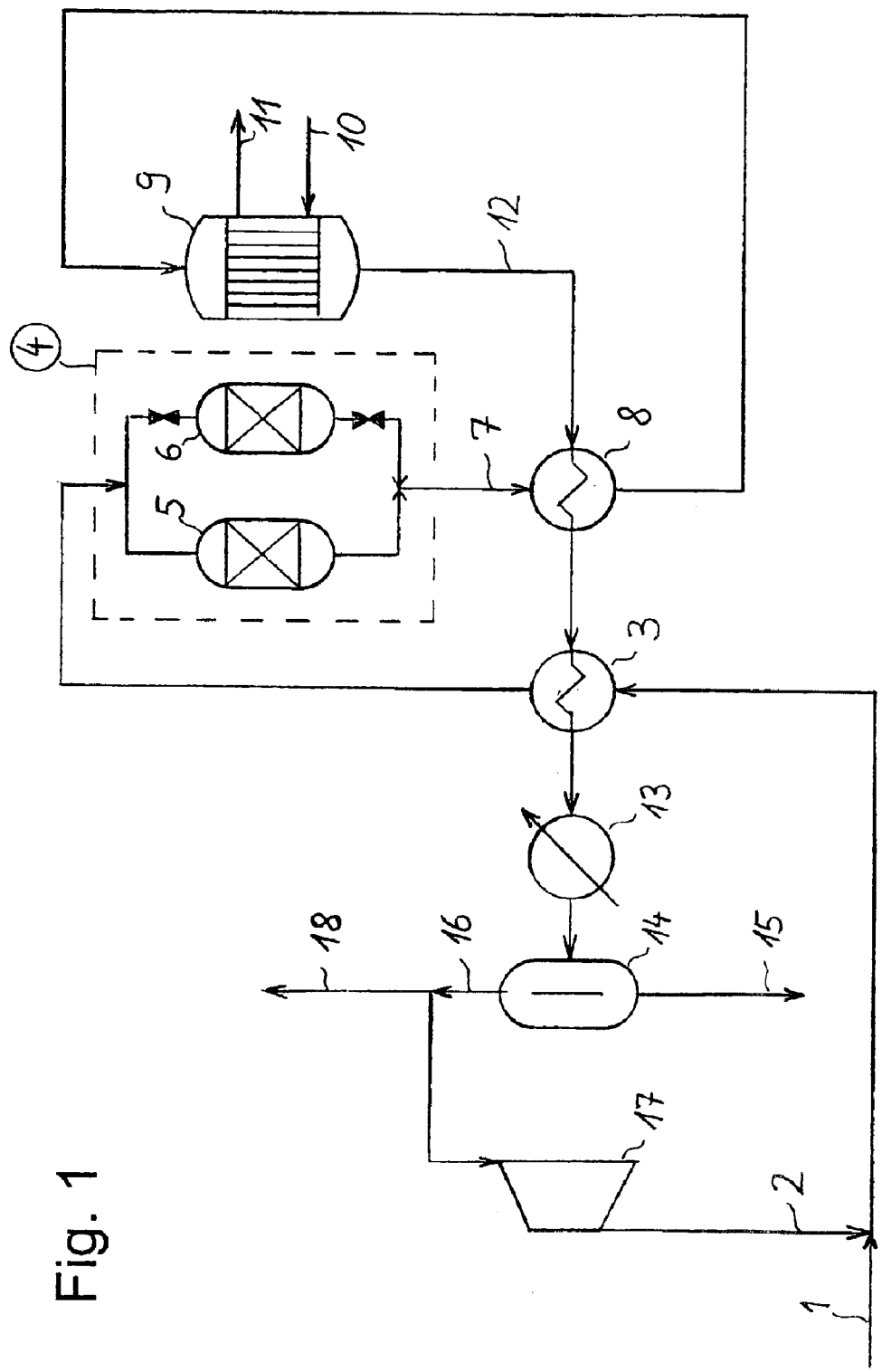
FIG. 1 shows the process designed in accordance with the invention and implemented in a loop-operated unit for the production of methanol, with a heat-shift system on the synthesis gas side, an absorption stage and a methanol synthesis reactor with integrated steam generation. The said diagram neither shows the production, dehydration and primary purification of the synthesis gas nor the compression unit required to obtain the synthesis pressure and the purification steps needed for the methanol produced.

Pre-compressed, fresh synthesis gas 1 is mixed with cycle synthesis gas 2 so that the latter has a temperature of approx. 77° C. Heat exchanger 3 is used to heat the cycle synthesis gas to approx. 160° C. and said gas is then sent to the absorption stage 4. This example provides for absorption stage 4 which consists of two bulk material vessels 5 and 6 for the catalyst packing in accordance with the invention. While the cycle synthesis gas flows through vessel 5 from top to bottom and the catalytic poisons are absorbed by the catalyst inventory, no gas stream flows through vessel 6 which also contains a catalyst inventory and which is shown by shut-off valves at the gas inlet and outlet, hence said vessel 6 is in stand-by mode. At an almost unchanged temperature, the purified cycle synthesis gas 7 is sent to heat exchanger 8 where it is heated to approx. 220° C., i.e. the temperature required for the synthesis, and it is then fed directly to methanol synthesis reactor 9. This is where the catalytic conversion to methanol takes place, the methanol being obtained in the form of gas at the temperature and synthesis pressure applied. The enormous reaction heat is transferred to the boiler feed water 10 which, for example, passes through the reactor shell, thus generating steam 11. The methanol concentration in the residual synthesis gas 12 usually ranges from 4 to 10 molar %. Said methanol-bearing synthesis gas 12 is cooled in a counter-current of cycle synthesis gas in heat exchangers 8 and 3. The gaseous methanol then condenses in condenser 13 and separates from the residual synthesis gas 16 in methanol separator 14 so that it is obtained as crude methanol. Part of the residual synthesis gas 16 is recompressed by cycle gas compressor 17 and recycled as recycle gas to the synthesis loop while the other part is discharged from the synthesis recycle system as purge gas 18 to inhibit a concentration of inert constituents.

LIST OF REFERENCES USED

1 Fresh synthesis gas
2 Cycle synthesis gas
3 Heat exchanger
4 Absorption stage
5 Vessel for bulk material
6 Vessel for bulk material
7 Purified synthesis gas
8 Heat exchanger
9 Methanol synthesis reactor
10 Boiler feed water
11 Steam
12 Methanol-bearing synthesis gas
13 Condenser
14 Methanol separator
15 Crude methanol
16 Residual synthesis gas
17 Recycle gas compressor
18 Purge gas

What is claimed is:

1. A process for the catalytic production of methanol under pressure using a synthesis gas which at least contains hydrogen, carbon monoxide, carbon dioxide and also undesired impurities, with at least one stage being equipped with a rector, wherein an absorption stage is connected upstream of each catalytic reaction system for the production of methanol, which contains, suitable catalyst material as absorbent for the synthesis of methanol, the absorption stage being operated at a temperature which is below the temperature required for the catalytic conversion to methanol.

2. The process according to claim 1, wherein a catalyst material with a composition of 30 to 50% CuO, 30 to 50% ZnO and 10 to 30% $Al_2O_3$ is used as the absorbent.

3. The process according to claim 1, wherein an absorption temperature ranging from 100° C. to 200° C. is set in the absorption stage.

4. A unit for running the catalytic methanol production according to claim 1, wherein the absorption stage is designed as a simple cylindrical vessel with internals accommodating the catalyst inventory, with radial or axial gas flow, and is provided with one gas inlet and one gas outlet at each end as well as with a catalyst feed and discharge facility.

5. The unit according to claim 4, comprising two parallel-connected vessels, each of which can be shut off independently of the other on the gas side and which allow filling and discharge of one vessel with catalyst material while the other vessel remains in operation as required for the intended use.

6. The process according to claim 3, wherein an absorption temperature ranging from 150° C. to 160° C. is set in the absorption stage.

* * * * *

UNITED STATES PATENT AND TRADEMARK OFFICE
CERTIFICATE OF CORRECTION

PATENT NO.    : 6,894,081 B2
DATED         : May 17, 2005
INVENTOR(S)   : Hans-Joachim Bähnisch It is certified that error appears in the above-identified patent and that said Letters Patent is hereby corrected as shown below:

<u>Title page,</u>
Items [12] and [75], replace with the following:
-- [12] United States Patent
      Bähnisch

[75] Inventor: Hans-Joachim Bähnisch, Dortmund (DE) --.

Signed and Sealed this

Fifteenth Day of November, 2005

JON W. DUDAS
*Director of the United States Patent and Trademark Office*